United States Patent
Borja et al.

(10) Patent No.: US 9,198,416 B2
(45) Date of Patent: Dec. 1, 2015

(54) METHOD FOR ENHANCING DROUGHT TOLERANCE IN PLANTS

(71) Applicants: Marisé Borja, Madrid (ES); Julio Bonet-Gigante, Madrid (ES); Antonio Molina, Madrid (ES); Rafael Catalá, Madrid (ES); Julio Salinas, Madrid (ES)

(72) Inventors: Marisé Borja, Madrid (ES); Julio Bonet-Gigante, Madrid (ES); Antonio Molina, Madrid (ES); Rafael Catalá, Madrid (ES); Julio Salinas, Madrid (ES)

(73) Assignees: Plant Response Biotech S.L., Madrid (ES); Consejo Superior De Investigaciones Cientificas, Madrid (ES)

(*) Notice: Subject to any disclaimer, the term of this patent is extended or adjusted under 35 U.S.C. 154(b) by 12 days.

(21) Appl. No.: 14/203,261

(22) Filed: Mar. 10, 2014

(65) Prior Publication Data

US 2015/0052640 A1    Feb. 19, 2015

Related U.S. Application Data

(63) Continuation-in-part of application No. 14/142,285, filed on Dec. 27, 2013.

(60) Provisional application No. 61/865,549, filed on Aug. 13, 2013.

(51) Int. Cl.
*A01N 25/02* (2006.01)
*A01N 33/24* (2006.01)
(Continued)

(52) U.S. Cl.
CPC . *A01N 33/24* (2013.01); *A01C 1/06* (2013.01); *A01H 5/10* (2013.01); *A01N 25/00* (2013.01); *A01N 25/02* (2013.01); *A01N 37/44* (2013.01); *A01N 41/08* (2013.01); *C12N 15/82* (2013.01)

(58) Field of Classification Search
None
See application file for complete search history.

(56) References Cited

U.S. PATENT DOCUMENTS

| 6,455,468 B1 | 9/2002 | Li et al. |
| 6,762,052 B1 | 7/2004 | Cashman et al. |

(Continued)

FOREIGN PATENT DOCUMENTS

| ES | 2347399 A1 | 10/2010 |
| WO | 95/35022 A1 | 12/1995 |

(Continued)

OTHER PUBLICATIONS

Trimethylamine. Chemical Entities of Biological Interest. 2014. pp. 1-4.*

(Continued)

*Primary Examiner* — Anne Kubelik
*Assistant Examiner* — Ashley K Buran
(74) *Attorney, Agent, or Firm* — Bethany R. Roahrig; Barbara Campbell; Cochran Freund & Young, LLC

(57) ABSTRACT

A method for increasing drought tolerance in a plant or photosynthetic organism is provided, where the tolerance is increased by applying an effective amount of trimethylamine N-oxide (TMAO) or trimethylamine N-oxide di-hydrate, or a TMAO chemical derivative, or a TMAO chemical analog and thereof to a plant, seed or photosynthetic organism that has been exposed to or to be exposed to water stress conditions. Water stress tolerant plants or photosynthetic organisms produced through the application of trimethylamine N-oxide (TMAO) or trimethylamine N-oxide di-hydrate, or a TMAO chemical derivative, or a TMAO chemical analog to a plant or photosynthetic organism are also disclosed.

26 Claims, 1 Drawing Sheet

(51) Int. Cl.
| | |
|---|---|
| A01C 1/06 | (2006.01) |
| A01H 5/10 | (2006.01) |
| A01N 25/00 | (2006.01) |
| A01N 37/44 | (2006.01) |
| A01N 41/08 | (2006.01) |
| C12N 15/82 | (2006.01) |

(56) References Cited

U.S. PATENT DOCUMENTS

| | | | |
|---|---|---|---|
| 2007/0124833 A1 | 5/2007 | Abad et al. | |
| 2012/0084881 A1* | 4/2012 | Vriezen et al. | 800/278 |
| 2013/0130902 A1* | 5/2013 | Roose et al. | 504/187 |
| 2013/0333068 A1 | 12/2013 | Coffin | |
| 2015/0052632 A1* | 2/2015 | Borja et al. | 800/278 |

FOREIGN PATENT DOCUMENTS

| | | | | |
|---|---|---|---|---|
| WO | 96/41532 A1 | 12/1996 | | |
| WO | 97/08951 A1 | 3/1997 | | |
| WO | WO2008023263 | 2/2008 | | |
| WO | 2008/060555 A2 | 5/2008 | | |
| WO | WO2010034862 | 4/2010 | | |
| WO | WO 2010034862 | 4/2010 | | |
| WO | WO-2010034862 A1 * | 4/2010 | | A01H 3/04 |
| WO | 2015/022365 A1 | 2/2015 | | |

OTHER PUBLICATIONS

Hangzhou King Technica Technology Co., Ltd. TMAO (Trimethylamine N-oxide Dihydrate). Product Listing. 2006. p. 1.*
University of California Sonoma County Master Gardeners. Very drought tolerant plants. 2015. http://ucanredu/sites/scmg/Sonoma__Gardener__Articles/Very__Drought__Tolerant__Plants/#. pp. 1-2.*
Albert, S. Vegetable seeds per ounce/per gram. Harvest to Table. 2011. http://www.harvesttotable.com/2011/05/vegetable_seeds_per__ounce_per/. pp. 1-4.*
Ruiz de Galarreta. PI 665406. Centro de Investigacion y Mejora Agraria. 2012. pp. 1-2.*
Mohammadkhani et al. Water stress induced by polyethylene glycol 600 and sodium chloride in two maize cultivars. Pakistan Journal of Biological Sciences. 2008. 11(1): 92-97.*
Yancey, P.H., J. Exp. Biol., (2005), 208(15): 2819-30.
Li, J. et al., Plant Physiol., (2008), 148 (3):1721-33.
Schlaich, N.L., Trends Plant Sci., (2007), 12 (9): 412-8.
Hibino, T. et al., J. Biol. Chem., (2002), 277 (44): 41352-60.
Schlenk, D. et al., Biochem. Pharmacol., (1996), 52 (5): 815-8.
Lang, D. H. et al., Biochem. Pharmacol., (1998), 56 (8): 1005-12.
Larsen, B.K. et al., J. Comp. Physiol. B., (2001), 171 (50): 421-29.
Doan-Nguyen, V. et al., Protein Sci., (2007), 16(1): 20-29.
Cushman, J.C., Amer. Zool., (2001), 41(4): 758-769.
Lawton, M. P. et al., Arch. Biochem. and Biophysics., (1994) 308 (1) 254-257.
O'Donnell et al., Plant Physiology and Biochemistry., (2013) vol. 73: 83-92.
Fan et al., Trees. (1997) vol. 11: 342-348.
Mondal et al., J. Phys. Chem. B. (2013) vol. 117: 8723-8732.
Yang et al. Journal of Experimental Botany,(2010) vol. 61, No. 12, pp. 3245-3258.
Ashraf, M. and Foolad, M.R., Roles of glycine betaine and proline in improving plant abiotic stress resistance, Environmental and Experimental Biology, 2007, pp. 206-216, vol. 59.
Mäkelä, P. et al., Foliar application of glycinebetaine—a novel product from sugar beet—as an approach to increase tomato yield, Industrial Crops and Products, 1998, pp. 139-148, vol. 7.
Ibrahim, M. et al., Four foliar applications of glycinebetaine did not alleviate adverse effects of salt stress on growth of sunflower, Pak. J. Bot., 2006, pp. 1561-1570, vol. 38(5).
Agboma, P.C., et al., Exogenous glycinebetaine enhances grain yield of maize, sorghum and wheat grown under two supplementary watering regimes, J. Agronomy & Crop Science, 1997, pp. 29-37, vol. 178.
Agboma, P.C. et al., Effect of foliar application of glycinebetaine on yield components of drought-stressed tobacco plants, Expl. Agric., 1997, pp. 345-352, vol. 33.
Agboma, P.C. et al., an evaluation of the effect of exogenous glycinebetaine on the growth and yield of soybean: timing of application, watering regimes and cultivars, Field Crops Research, 1997, pp. 51-64, vol. 54.
Meek, C., Oosterhuis, D., and Gorham, J., Does foliar-applied glycine betaine affect endogenous betaine levels and yield in cotton? Crop Management, 2003, Abstract.
Mäkelä, P. et al., Uptake and translocation of foliar-applied glycinebetaine in crop plants, Plant Science,1996, pp. 221-230, vol. 121.
Kim, J. I., et al., Overexpression of Arabidopsis YUCCA6 in Potato Results in High-Auxin Developmental phenotypes and enhanced resistance to water deficit, Sep. 17, 2012, pp. 337-349, vol. 6(2).
Charrier, A. et al., The effect of carnitine on Arabidopsis development and recovery in salt stress conditions, Planta, Aug. 19, 2011, pp. 123-135, vol. 235(1).
Lee, M. et al., Activation of a flavin monooxygenase gene YUCCA7 enhances drought resistance in Arabidopsis, Nov. 23, 2011, pp. 923-938, vol. 235(5).

* cited by examiner

METHOD FOR ENHANCING DROUGHT TOLERANCE IN PLANTS

CROSS REFERENCE TO RELATED APPLICATIONS

This application is a continuation-in-part patent application and claims priority to U.S. application Ser. No. 14/142,285, filed on Dec. 27, 2013, the entire contents of which are incorporated herein by reference for all purposes and is a U.S. non-provisional patent application of and claims the benefit of U.S. Provisional Application No. 61/865,549, filed Aug. 13, 2013, the entire contents of which are incorporated herein by reference for all purposes.

JOINT RESEARCH AGREEMENT

The claimed invention was made by parties to a joint research agreement, within the meaning of 35 U.S.C. 100(h), which was in effect before the effective filing date of the application, and the claimed invention was made as a result of activities undertaken within the scope of the joint research agreement. The parties of the joint research agreement are the State Agency Council for Scientific Research (CSIC), the Institute of National Agricultural Research and Technology and Food (INIA), and Plant Response Biotech, S.L.

BACKGROUND

All publications cited in this application are herein incorporated by reference.

When plants are exposed to conditions where reduced water content in the soil due to a shortage of rainfall or irrigation leads to impaired water absorption, what could be called drought stress conditions, physiological functions of cells may deteriorate and thus various disorders may arise in the plant. When subjected to such stress factor plants display a variety of mechanistic responses as protective measures, with a resultant adverse effect on growth, development, and productivity. Significant losses in quality and yield are commonly observed.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope.

An embodiment of the present invention may comprise a method for producing a water stress tolerant plant or photosynthetic organism comprising: applying an effective amount of Trimethylamine N-oxide (TMAO), TMAO di-hydrate, TMAO chemical derivative, or a TMAO chemical analogue, for example, an alquil amine oxide, to a plant, plant part, photosynthetic organism or a seed; and growing the plant, plant part, photosynthetic organism or a seed, wherein a water stress tolerant plant or photosynthetic organism is produced.

An embodiment of the present invention may comprise a water stress tolerant plant or photosynthetic organism produced from applying an effective amount of TMAO, TMAO dihydrate, a TMAO chemical derivative, or a TMAO chemical analogue to a plant, plant part, photosynthetic organism or a seed and growing the plant, plant part, photosynthetic organism or a seed.

Various embodiments are set forth in the Detailed Description as provided herein and as embodied by the claims. It should be understood, however, that this Summary does not contain all of the aspects and embodiments of the present invention, is not meant to be limiting or restrictive in any manner, and that the invention(s) as disclosed herein is/are understood by those of ordinary skill in the art to encompass obvious improvements and modifications thereto.

Additional advantages of the present inventions will become readily apparent from the following discussion, particularly when taken together with the accompanying drawings and sequence listings.

BRIEF DESCRIPTION OF THE FIGURE

The accompanying FIGURE, which is incorporated herein and form a part of the specification, illustrate some, but not the only or exclusive, example embodiments and/or features. It is intended that the embodiments and FIGURE disclosed herein are to be considered illustrative rather than limiting.

FIG. 1 shows, from the left, tomato plants irrigated with water and on the right, plants irrigated with 5.5 g/L TMAO di-hydrate after drought recovery.

DETAILED DESCRIPTION OF THE EMBODIMENTS

Embodiments of the present disclosure include methods for producing plants or photosynthetic organisms tolerant to water stress, including tolerances to but not limited to drought, excessive moisture as well as efficient water usage where normal yields are produced with less water input. These methods include the application of organic compounds, such as trimethylamine N-oxide ("TMAO") or a TMAO analog, a TMAO derivative, or TMAO di-hydrate to plants or seeds to produce a plant tolerant to water stress. The present disclosure also includes plants or photosynthetic organisms tolerant to water stress, including tolerances to but not limited to drought and excessive moisture. These water stress tolerant plants and photosynthetic organisms may be produced through the application of organic compounds, such as trimethylamine N-oxide ("TMAO") or a TMAO analog, a TMAO derivative, or TMAO di-hydrate to induce water stress tolerance, allowing for the production of plants and photosynthetic organisms with more biomass when compared to plants and photosynthetic organisms that have not been treated with organic compounds to produce water stress tolerance.

As used herein the term "water stress" includes drought stress, excessive moisture stress or efficient water usage where normal yields are produces with less water input. The term "drought stress" as used herein can be induced in plants under conditions where reduced water content in the soil, due to a shortage of rainfall or irrigation, leads to impaired or reduced water absorption by the plant or photosynthetic organism. The term "excessive moisture" can be induced in plants or other photosynthetic organisms where excessive water content of the soil also leads to impaired water absorption by the plant or other photosynthetic organisms. The term "efficient water use" may be applied to a plant that is induced to produce normal yields under conditions where less water than is customary or average for an area or a plant is applied to a plant. Water stress may trigger in plants a deterioration of physiological functions of cells, thereby leading to various disorders. While the conditions which induce drought stress may vary depending on the kind of the soil where plants are cultivated, examples of the conditions include but are not limited to: a reduction in the water content in the soil of 15% by weight or less, more severely 10% by weight or less, and still more severely 7.5% by weight or less; or the pF value of the soil of 2.3 or more, more severely 2.7 or more, and still more severely 3.0 or more.

While it has been known that phytohormones and some chemical substances such as plant growth regulators have effects on plants in reducing water stress such as drought stress or excessive moisture stress (see *Journal of Plant Growth Regulation* (2010) 29: 366-374), those effects are not necessarily satisfactory in practice. For example, organic osmolytes are small solutes used by cells of numerous water-stressed organisms and tissues to maintain cell volume. Similar compounds are accumulated by some organisms in anhydrobiotic, thermal and possibly pressure stresses. These solutes are amino acids and derivatives, polyols and sugars, methylamines, methylsulfonium compounds and urea. Except for urea, they are often called "compatible solutes", a term indicating lack of perturbing effects on cellular macromolecules and implying interchangeability. However, these features may not always exist, and the practical use cannot be taken for granted since high levels might cause overstabilization of proteins and some protective properties of osmolytes are harmful in the absence of a perturbant to offset (Yancey, P. H. (2005). *J. Exp. Biol.* 208 (Pt 15): 2819-30). For example the osmolite glycinebetaine (betaine) affords osmoprotection in bacteria, plants and animals, and protects cell components against harsh conditions in vitro, however, engineering of betaine production in three diverse species lacking it, *Arabidopsis, Brassica napus*, and tobacco (*Nicotiana tabacum*), by constitutive expression of a bacterial choline oxidase gene only conferred a moderate stress tolerance in some but not all betaine-producing transgenic lines and the responses to stresses such as salinity, drought, and freezing were variable among the three species. Furthermore, a fitness cost was observed in the three species (Jun H, Hariji et al. (2000) *Plant Physiol.* 122: 747-56).

As introduced above, an embodiment of the present disclosure provides one or more methods for producing plants or photosynthetics organisms tolerant to water stress, including but not limited to drought tolerance or excessive moisture, in plants wherein an application of trimethylamine N-oxide or "TMAO", wherein TMAO includes but is not limited to, TMAO di-hydrate, TMAO chemical derivative, or a TMAO chemical analogue, to a plant or seed to reduce water stress in the plant when the plant is exposed to water stress conditions. Further methylamines (e.g. trimethylamine N-oxide (TMAO)) can enhance protein folding and ligand binding and counteract perturbations by urea (e.g. in elasmobranchs and mammalian kidney), inorganic ions, and hydrostatic pressure in deep-sea animals (Yancey, 2005).

The one or more methods of producing a plant or photosynthetic organism tolerant to water stress is applicable to a variety of plants including monocotyledonous or dicotyledonous plants, including but not limited to transgenic plants. As used herein, transgenic plants include plants, or photosynthetic organism, which have been genetically modified to contain DNA constructs as will be discussed further herein. The methods for producing a plant or organism tolerant to water stress may be applicable to the whole plant or organism or a part of a plant, for example in an organ, tissue, a cell or a part of a plant cell, for example in an organelle, which comprises introducing into, and expressing in, the plant or plant cell a nucleic acid which codes for a monooxygenase or FMO protein, and which mediates an increased production of endogenous TMAO and therefore a water stress tolerance, such as an increased tolerance to drought or an increased tolerance to excessive moisture.

One or more embodiments described herein may further provide methods for producing a water stress tolerant plant or photosynthetic organism which comprises applying an effective enough amount of TMAO to a plant or organism that has been exposed to or to be exposed to water stress conditions. This method may further include a seed treatment application, a spray treatment or an irrigation treatment of the TMAO. As an example an effective amount of TMAO seed treatment may include a seed treatment of TMAO in an amount from 0.1 to 1000 g per 100 kg seeds or 0.1 to 100 g per liter of spray treatment or irrigation treatment. The use of TMAO, TMAO dehydrate, a TMAO derivative or chemical analogue and agriculturally acceptable salts, wherein agriculturally acceptable salts may include but is not limited to, a mixture of ammonium phosphate, ammonium nitrate, potassium nitrate, and calcium nitrate in a 2-2-1-1 proportion for reducing water stress in a plant.

Water stress in plants produced using the methods of treatment of TMAO described herein may be recognized or identified by comparing a change in plant phenotypes described in more detail below between plants which have been exposed to water stress conditions and plants which have not been exposed to the same water stress conditions. Water stress in a plant or photosynthetic organism may be indicated by a change in one or more of the following plant phenotypes, which can serve as indicators of the water stress in plants: (1) germination percentage, (2) seedling establishment rate, (3) number of healthy leaves, (4) plant length, (5) plant weight, (6) leaf area, (7) leaf color, (8) number or weight of seeds or fruits, (9) quality of harvests, (10) flower setting rate or fruit setting rate, (11) chlorophyll fluorescence yield, (12) water content, (13) leaf surface temperature, and (14) transpiration capacity.

Water stress may be quantified as the "intensity of stress" where intensity of stress is represented as following: "Intensity of stress"=100× "any one of plant phenotypes in plants which have not been exposed to water stress"/"the plant phenotype in plants which have been exposed to water".

The methods described herein are applied to plants that have been exposed to or to be exposed to water stress conditions whose intensity of stress represented by the above equation is from 105 to 450, preferably from 110 to 200, and more preferably from 115 to 160. In a plant exposed to water stress conditions, an influence may be recognized on at least one of the above phenotypes. That is, observed as: (1) decrease in germination percentage, (2) decrease in seedling establishment rate, (3) decrease in number of healthy leaves, (4) decrease in plant length, (5) decrease in plant weight, (6) decrease in leaf area increasing rate, (7) leaf color fading, (8) decrease in number or weight of seeds or fruits, (9) deterioration in quality of harvests, (10) decrease in flower setting rate or fruit setting rate, (11) decrease in chlorophyll fluorescence yield, (12) decrease in water content, (13) increase in leaf surface temperature, or (14) decrease in transpiration capacity, among others, and the magnitude of the water stress in the plant can be measured using that as an indicator.

The methods described herein are directed to methods for reducing water stress in a plant or organism by producing a plant or organism tolerant to water stress by applying the TMAO to the plant that has been exposed to or will be exposed to water stress conditions. The effect of reducing the water stress of a plant can be evaluated by comparing the above phenotypic indicators between a plant treated with TMAO and a plant which has not been treated with TMAO after the plants or organisms are exposed to water stress conditions. Stages in which plants or organisms treated with TMAO can be exposed to the water stress conditions include all growth stages of plants, including a germination period, a vegetative growing period, a reproductive growing period and a harvesting period. The application period of the TMAO as used herein may be any growth stage of plants or organisms, and examples thereof include the germination period such as before seeding, at the time of seeding, and after seeding and before or after emergence; the vegetative growing period such as at the time of seedling raising, at the time of seedling transplantation, at the time of cutting or sticking, or at the time of growing after settled planting; the reproductive growing period such as before blooming, during blooming, after blooming, immediately before earing or during the ear formation period; and the harvesting period such as before harvesting plan, before ripening plan, or a coloration initiation period of fruits. Plants to which TMAO is to be applied may be plants which have been exposed to or will be exposed to the water stress conditions. That is, the compound can also be preventively applied to plants before being exposed to the water stress conditions in addition to plants which have been exposed to the water stress conditions.

The TMAO used in the methods described herein can be used alone, or in combination with various inert ingredients such as solid carriers, liquid carriers, and surfactants as described hereinafter.

Examples of a solid carrier used in formulation with TMAO may include powders, fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; and synthetic inorganic materials such as synthetic hydrated silicon oxide.

Examples of a liquid carrier may include aromatic hydrocarbons such as xylene, alkylbenzene and methylnaphthalene; alcohols such as 2-5 propanol, ethyleneglycol, propylene glycol, and ethylene glycol monoethyl ether; ketones such as acetone, cyclohexanone and isophorone; vegetable oil such as soybean oil and cotton seed oil; and petroleum aliphatic hydrocarbons, esters, dimethylsulfoxide, acetonitrile and water.

Examples of a surfactant include anionic surfactants such as alkyl sulfonate ester salts, alkylaryl sulfonate salts, dialkyl sulfosuccinate salts, polyoxyethylene alkyl aryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters; and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminium magnesium silicate and alumina sol, preservatives, colouring agents and stabilization agents such as PAP (acid phosphate isopropyl) and butylated hydroxytoluene (BHT).

The methods for production of a plant or photosynthetic organism tolerant to water stress as described herein may be carried out by applying an effective amount of the TMAO to plants or growing sites of plants. As used herein an effective amount of TMAO may include a range from 0.1 to 1.000 g per liter per 1-10 kg seeds. When incorporated into the entire soil, an effective amount of TMAO may range from 0.1 to 1.000 g or 1 to 500 g, per 1.000 $m^2$ of soil. When treatment with TMAO is used as an emulsion, a wettable powder, a flowable agent, or a microcapsule may be used for the treatment by spraying the plant after dilution with water. In this case, the concentration of the TMAO may range from 0.01 to 10,000 ppm, or from 1 to 5,000 ppm. A dust formulation and a granule of TMAO may be used for the treatment of water stress without dilution of the TMAO. In the treatment of seeds or the treatment of bulbs, an example of the weight of the TMAO per 100 kg of seeds may range from 0.1 to 100 g, as well as from 1 to 30 g. Examples of the seeds or bulbs used in the methods described herein include those having a weight of 100 g or less, including 20 g or less, 0.5 g or less, as well as 50 mg or less. In the treatment of seedlings, an example of the weight of the TMAO per seedling may range from 0.01 to 20 mg, including 0.5 to 8 mg. In the treatment of the soil before or after sowing seedlings, the weight of the TMAO per 1.000 $m^2$ may range from 0.1 to 1000 g, including from 10 to 100 g.

TMAO may be applied to a variety of plants in various forms or sites, such as foliage, buds, flowers, fruits, ears or spikes, seeds, bulbs, stem tubers, roots and seedlings. As used herein, bulbs mean discoid stem, rhizomes, root tubers, and rhizophores. In the present specification, TMAO may also be applied to cuttings and sugar cane stem cuttings.

The following are examples of the growing sites of plants include soil before or after sowing plants. When the TMAO is applied to plants or growing sites of plants, the TMAO is applied to the target plants once or more. TMAO may be applied as a treatment to foliage, floral organs or ears or spikes of plants, such as foliage spraying; treatment of seeds, such as seed sterilization, seed immersion or seed coating; treatment of seedlings; treatment of bulbs; and treatment of cultivation lands of plants, such as soil treatment. The TMAO may be applied only to specific sites of plants, such as floral organ in the blooming season including before blooming, during blooming and after blooming, and the ear or spike in the earing season, or may be applied to entire plants.

TMAO may be applied as a soil treatment in the form a spray onto soil, soil incorporation, and perfusion of a chemical liquid into the soil (irrigation of chemical liquid, soil injection, and dripping of chemical liquid). The placement of TMAO during soil treatment includes but is not limited to planting hole, furrow, around a planting hole, around a furrow, entire surface of cultivation lands, the parts between the soil and the plant, area between roots, area beneath the trunk, main furrow, growing box, seedling raising tray and seedbed, seedling raising. TMAO soil treatment may be before seeding, at the time of seeding, immediately after seeding, raising period, before settled planting, at the time of settled planting, and growing period after settled planting.

When applying TMAO as a soil treatment, two or more kinds of TMAOs may be simultaneously applied to the plant, for example, TMAO and TMAO di-hydrate, or TMAO di-hydrate and an aryl amine oxide, or a solid fertilizer such as a paste fertilizer containing the TMAO may be applied to the soil. TMAO may be mixed in an irrigation liquid, and, examples thereof include injecting to irrigation facilities (irrigation tube, irrigation pipe, sprinkler, etc.), mixing into the flooding liquid between furrows, mixing into a hydroponic medium and the like.

Alternatively, an irrigation liquid may be mixed with the TMAO in advance and, for example, used for treatment by an appropriate irrigating method including the irrigation method mentioned above and the other methods such as sprinkling and flooding. TMAO may also be applied by winding a crop with a resin formulation processed into a sheet or a string, putting a string of the resin formulation around a crop so that the crop is surrounded by the string, and/or laying a sheet of the resin formulation on the soil surface near the root of a crop.

In another embodiment, TMAO may be used for treating seeds or bulbs as well as a TMAO spraying treatment for seeds in which a suspension of TMAO is atomized and sprayed on a seed surface or bulb surface. A smearing treatment may also be used in where a wettable powder, an emulsion or a flowable agent of the TMAO is applied to seeds or bulbs with a small amount of water added or applied as is without dilution. In addition, an immersing treatment may be used in which seeds are immersed in a solution of the TMAO for a certain period of time, film coating treatment, and pellet coating treatment.

TMAO may be used for the treatment of seedlings, including spraying treatment comprised of spraying the entire seedlings with a dilution having a proper concentration of active ingredients prepared by diluting the TMAO with water. As with seed treatment, an immersing treatment may also be used comprised of immersing seedlings in the dilution, and coating treatment of adhering the TMAO formulated into a dust formulation to the entire seedlings.

TMAO may be treated to soil before or after sowing seedlings including spraying a dilution having a proper concentration of active ingredients prepared by diluting TMAO with water and applying the mixture to seedlings or the soil around seedlings after sowing seedlings. A spray treatment of TMAO formulated into a solid formulation such as a granule to soil around seedlings at sowing seedlings may also be used.

TMAO may be used for treatment of hydroponics. Examples may include dissolving or suspending TMAO in a conventionally used culture medium for hydroponics, at a concentration within a range from 0.0001 to 10 g/liter.

TMAO may be used at the time of tissue culture or cell culture of a plant to promote tolerance to water stress. TMAO may be dissolved or suspended in a conventionally used culture medium for plant tissue culture or other organisms, such as a Murashige and Skoog ("MS") culture medium. Examples may include a concentration within a range from 0.0001 to 10 g/liter. In this case, in accordance with a usual method, saccharides as a carbon source, various phytohormones and the like can be appropriately added.

A variety of seeds or bulbs may be used in the methods described herein including but are not limited to plants in the families' Solanaceae and Cucurbitaceae, as well as plants selected from the plant genera *Calibrachoa, Capsicum, Nicotiana, Nierembergia, Petunia, Solanum, Cucurbita, Cucumis, Citrullus, Glycine*, such as *Glycine max* (Soy), *Calibrachoa×hybrida, Capsicum annuum* (pepper), *Nicotiana tabacum* (tobacco), *Nierenbergia scoparia* (cupflower), *Petunia xhybrida, Solanum lycopersicum* (tomato), *Solanum tuberosum* (potato), *Solanum melongena* (eggplant), *Cucurbita maxima* (squash), *Cucurbita pepo* (pumpkin, zucchini), *Cucumis metuliferus* (Horned melon) *Cucumis melo* (Musk melon), *Cucumis sativus* (cucumber) and *Citrullus lanatus* (watermelon). Various monocotyledonous plants, in particular those which belong to the family Poaceae, may be used with the methods described herein, including but not limited to, plants selected from the plant genera *Hordeum, Avena, Secale, Triticum, Sorghum, Zea, Saccharum, Oryza, Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugarcane) and *Oryza sativa* (rice). Additional examples of plants in which water stress may be produced using the methods described herein include the followings. crops: buckwheat, beet, canola, rapeseed, sunflower, sugar cane, tobacco, and pea, etc.; vegetables: solanaceous vegetables such as paprika and potato; cucurbitaceous vegetables; cruciferous vegetables such as Japanese radish, white turnip, horseradish, kohlrabi, Chinese cabbage, cabbage, leaf mustard, broccoli, and cauliflower, asteraceous vegetables such as burdock, crown daisy, artichoke, and lettuce; liliaceous vegetables such as green onion, onion, garlic, and asparagus; ammiaceous vegetables such as carrot, parsley, celery, and parsnip; chenopodiaceous vegetables such as spinach, Swiss chard; lamiaceous vegetables such as *Perilla frutescens*, mint, basil; strawberry, sweet potato, *Dioscorea japonica, colocasia*; flowers; foliage plants; grasses; fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, tangerine, lemon, lime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidata*). Examples of plants in which water stress tolerance may be produced may include rice, corn, canola, soybean and wheat. The aforementioned "plants" include transgenic plants, expressing other gene traits.

As used herein, "plants" means all dicotyledonous or monocotyledonous plants, including but is not limited to annual and perennial dicotyledonous or monocotyledonous plants and includes by way of example, but not by limitation, those of the genera *Glycine, Vitis, Asparagus, Populus, Pennisetum, Lolium, Oryza, Zea, Avena, Hordeum, Secale, Triticum, Sorghum, Saccharum* and *Lycopersicum*. The term plant may also include but not limited to the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. "Mature plants" means plants at any developmental stage beyond the seedling stage. Seedling means a young, immature plant in an early developmental stage.

Dicotyledonous plants includes but is not limited to the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

As used herein "photosynthetic organisms" may include but is not limited to organisms such as *Arthrospira* spp., *Spirulina* spp., *Synechococcus elongatus, Synechococcus* spp., *Synechosystis* spp., *Synechosystis* spp., and *Spirulina plantensis, Calothrix* spp., *Anabaena flosaquae, Aphanizomenon* spp., *Anabaena* spp., *Gleotrichia* spp., *Oscillatoria* spp. and *Nostoc* spp.; eukaryotic unicellular algae such as but not limited to *Chaetoceros* spp., *Chlamydomonas reinhardtii, Chlamydomonas* spp., *Chlorella vulgaris, Chlorella* spp.,

*Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantzschia* spp., *Hematococcus* spp., *Isochrysis* spp., *Laminaria* spp., *Nannochloropsis* spp., *Navicula* spp., *Nereocystis luetkeana*, *Pleurochrysis* spp., *Postelsia palmaeformis*, and *Sargassum* spp.

In another embodiment, one or more methods are provided for the production of a product described herein may comprise: a) growing the plants described herein or obtainable by the methods of described herein and b) producing the product from or by the plants of the invention and/or parts, e.g. seeds, of these plants.

In a further embodiment the method may comprise the steps a) growing the plants of the invention, b) removing the harvestable parts as defined above from the plants and c) producing the product from or by the parts of the transgenic plant or organism.

The water stress tolerant plants or organisms may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In another embodiment the products produced by the methods described herein are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the methods for the production are used to make agricultural products such as, but not limited to, plant extracts, proteins, amino acids, carbohydrates, fats, oils, polymers, vitamins, and the like. Please note that it is possible that a plant product consists of one or more agricultural products to a large extent.

An embodiment may further comprise a method for producing a plant or photosynthetic organism expressing or overexpressing one or more monooxygenase protein ("FMO") proteins coding sequences in said plant or photosynthetic organism, which comprises growing a plant or photosynthetic organism having an FMO protein stably integrated into said plant or photosynthetic organism's nuclear genome or said plant's chloroplast genome under conditions suitable for an expression or overexpression of the FMO protein in the plant or photosynthetic organism, wherein the expression or overexpression of the FMO protein coding sequence in said water stress tolerant photosynthetic organism catalyzes the oxidation of endogenous metabolites containing nucleophilic nitrogen.

An embodiment of the present invention may comprise a water stress tolerant plant or photosynthetic organism, wherein the water stress tolerant plant or photosynthetic organism overexpresses FMO proteins in the plant's or photosynthetic organism's nuclear genome or the plant's chloroplast genome.

The DNA construct for the expression or overexpression of an FMO protein coding sequences in photosynthetic organisms may comprise a promoter (such as a constitutive promoter for constitutive expression or an inducibler promoter for induced expression) and the FMO protein coding sequence, wherein the promoter is operably linked to the FMO protein coding sequence, where the FMO protein coding sequence may be selected from genes with the highest homologies to At1g12140 from *Solanum lycopersicum* SlFMO GS-OX1 (Solyc06g060610), SlFMO GS-OX2 (AK324297.1), *Vitis vinifera* VvFMO GS-OX3-1, VvFMO GS-OX3-2, VvFMO GS-OX3-3, *Populus trichocarpa* PtFMO-GS-OX3, PtFMO GS-OX2, PtFMO GS-OX1, *Oryza sativa* OsFMO-OX, *Glycine max* GmFMO, *Cucumus sativus* CsFMO GS-OX3-1, CsFMO GS-OX3-2, CsFMO GS-OX3-3, CsFMO GS-OX3-4, *Brassica rapa* subsp. *pekinensis* BrFMO GS-OX1, *Medicago* truncatula MtFMO GS-OX5, *Zea mays* ZmFMO, *Gossypium hirsutum* GhFMO-1, *Homo sapiens* HsFMO-3 and *Oryctolagus cuniculus* OcFMO-5

The practice described herein employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley-VCH (2005); Engelke, *RNA Interference (RNAi): The Nuts & Bolts of siRNA Technology*, DNA Press (2003); Gott, *RNA Interference, Editing, and Modification: Methods and Protocols* (*Methods in Molecular Biology*), Human Press, Totowa, N.J.

(2004); and Sohail, *Gene Silencing by RNA Interference: Technology and Application*, CRC (2004)).

EXAMPLES

The following examples are provided to illustrate further the various applications and are not intended to limit the invention beyond the limitations set forth in the appended claims.

General Methods

Biological Material and Growth Conditions

For each wilting or limited water experiment 480 seeds (of either pepper, barley, tomato, cucumber or corn) were sown, producing 384 plants in 512 cm$^3$ pots (4 plants per pot). Plants were grown under chamber conditions at 21° C. for 3 weeks. Then, the plants were moved to a greenhouse, where average temperature was 25° C. to 28° C. Treatments as described herein were done when the plants had two extended leaves and the next pair of leaves were coming up.

Treatments:

Twelve (12) pots (containing 48 plants) were irrigated with 40 ml of either: water, 0.1 g/L TMAO di-hydrate solution, 1.0 g/L TMAO di-hydrate solution, or 5.5 g/L TMAO di-hydrate solution. Another set of 12 pots containing 48 plants were sprayed with 40 ml of either water (3.3 ml in average per pot), a solution containing 0.1 g/L TMAO di-hydrate solution, 1.0 g/L TMAO di-hydrate, or 5.5 g/L TMAO di-hydrate. All pots were also watered with 40 ml of water. The sprayed plants were watered with the same volume of water as the "irrigated plants) The pots were located on plastic glass to maintain constant moisture and to avoid liquid spillage during watering. Trays containing the pots were located on greenhouse tables. The distribution of the trays on the table and the position on the pots in the tray was changed every week to avoid position effects.

After the treatments described above, the plants were not watered until the pots completely lost their moisture, taking about 4 to 8 days depending on the season, at which point the plants were extremely wilted for the extreme drought experiments. The plants were then watered once with solutions containing the different amounts of TMAO di-hydrate described above (0.1 g/L, 1.0 g/L or 5.5 g/L) or just water, after which the plants were left to lose their moisture completely again for three consecutive cycles of watering after wilting. For the "limited water" experiments they were watered with 20 ml of water or solution instead of 40 ml when the first plants started to wilt. The plant survival rate was recorded and analyzed for the "extreme drought" experiments in which plants were allowed to wilt severely before watering, while the stem length was recorded as analyzed for the limited water experiments in which the plants are watered with 30% of the water that the plant requires.

Strawberries

In order to determine the plant fruit productivity under normal conditions, 'Sabrina', 'Candonga' and 'Fortuna' variety strawberry plants were grown under standard strawberry production conditions and 120 plants of each variety per treatment (where the treatment was a Control comprising standard watering or 1 g/L of TMAO spray every four weeks) were analyzed. Plants were located in four (4) different positions for each group of 30 plants from the same treatment. Fruits were harvested from individual plants and total weight was determined for each plant.

Tomatoes

In order to determine the drought or water stress tolerance after seed treatments with TMAO di-hydrate and germination in the presence of TMAO di-hydrate, tomato 'Moneymaker' seeds were surface sterilized for 3 minutes in ethanol 70%, then rinsed twice and finally included in a pre-treatment solution of 0.1 g/L TMAO di-hydrate solution (or just water) under shaking for 3 hours. Then, they were rinsed and included in the germination plates under sterile conditions. Polyethylene glycol (PEG-6000) was added to the germination medium (Murashige and Skoog salts medium) at 152 and 182 g/L. The increasing amount of PEG reduces ψ (hydric potential) values, simulating drought conditions for germination. Each germination plate had at least 30 seeds, and each treatment/pretreatment plate was replicated five times (150 seeds per treatment/pretreatment). Seeds were left to germinate for 10 days under dark conditions in a culture chamber (21° C. light and 20° C. night, 65% humidity). Then, germinated seeds were recorded by visual inspection and data analysis was performed using Statgraphics software.

Nuclear Magnetic Resonance Spectroscopy (NMR)

TMAO content in plants was determined by harvesting three leaves per treatment and freezing them in liquid nitrogen before the NMR determination. At least three independent plants were treated per experiment.

Example 1

TMAO accumulates in pepper and barley after 1 week drought treatment. 'Murano' pepper and 'Bomi' barley seeds were sown and grown as described above. Control plants (six weeks old) were irrigated with 40 ml of water twice in the week, while "drought" treated plants were not irrigated. Leaves were harvested and TMAO was determined by NMR as described. As shown in Table 1, TMAO levels increase almost three fold compared to the control in both pepper and barley after drought treatment.

TABLE 1

TMAO accumulation after 1 week drought

| Crop | TMAO (uM) | SD | % Control |
|---|---|---|---|
| Pepper Control. | 446.68 | 215.86 | 100 |
| Pepper Drought 7 days | 1224.23 | 243.10 | 274 |
| Barley Control | 422.10 | 43.36 | 100 |
| Barley Drought 7 days | 1252.73 | 251.99 | 297 |

As shown in Table 1, in row 1, the control pepper shows 446.68 μM of TMAO, while in row 2 it is shown that 7 days of drought treatment increases TMAO levels in pepper 2.74 fold to 1224.23 μM. Analogously in row 3 control barley shows 422.10 μM of TMAO while in row 4 it is shown that 7 days of drought treatment increases TMAO levels in barley 2.97 fold to 1252.73 μM.

Example 2

TMAO accumulates in pepper and barley when applied exogenously. 'Murano' pepper seeds and 'Bomi' barley seeds were sown and grown as described above. Control plants (six weeks old) were sprayed with water and pepper treated plants were sprayed with 1 g/l of TMAO while barley plants were sprayed with 1 g/l of TMAO formulated with 0.1% of C8-C10 Alkylpolysaccharide. Leaves were harvested and TMAO was determined by NMR. The percentage of TMAO increase compared to untreated controls was determined for each time point. TMAO levels increase in pepper and barley with exogenous treatment of TMAO at 1 g/l to higher levels than drought treatment and furthermore, the TMAO levels are high up to 40 days post spray in pepper.

TABLE 2

TMAO accumulation after TMAO di-hydrate spray treatments

| Crop | % Control |
|---|---|
| Pepper 1 day post spray | 529 |
| Pepper 10 days post spray | 373 |
| Pepper 20 days post spray | 286 |
| Pepper 30 days post spray | 135 |
| Pepper 40 days post spray | 213 |
| Barley 1 day post spray | 822 |

As shown in Table 2, in row 1, pepper sprayed with TMAO increases its TMAO level 5.29 fold 1 day post spray when compared with control sprayed with water. The level decreases after 10 days to 3.73 fold of control (row 2), after 20 days to 2.86 fold of control (row 3), after 30 days to 1.35 fold of unsprayed control (row 4), staying above the water sprayed control even 40 days after spray (row 5). Analogously in row 6, barley sprayed with TMAO and an alkylpolysaccharide, increases its TMAO level 8.22 fold 1 day post spray when compared with control sprayed with just the alkypolisaccharide due to better penetration of the TMAO formulated with the alkylpolysaccharide.

Example 3

Exogenous application of TMAO di-hydrate does not have trade-offs in strawberry. Fruit yield was determined in 'Sabrina', 'Candonga' and 'Fortuna' strawberry plants treated with 1 g/l of TMAO di-hydrate or water as described above in order to evaluate the trade-off costs of the treatment with no water stress. However, no significant difference was observed in the fruit production which was always slightly higher in the TMAO di-hydrate treated plants.

TABLE 3

Strawberry fruit production after TMAO di-hydrate spray treatments every 4 weeks for 3 months

| Strawberry Variety | % Control |
|---|---|
| Sabrina | 106 |
| Candonga | 102 |
| Fortuna | 101 |
| Total | 105 |

Table 3, shows that TMAO can be applied exogenously for three months without a fitness cost. In row 1 the total production weight of Sabrina variety plants treated with TMAO di-hydrate produced 106% when compared with water treated controls, in row 2 the total production weight of Candonga variety plants treated with TMAO di-hydrate produce 102% when compared with controls, in row 3 the total production weight of Fortuna variety plants treated with TMAO di-hydrate produce 101% when compared with controls, while in row the total production weight of the three variety plants treated with TMAO di-hydrate produce 105% when compared with water treated controls of the three varieties.

Example 4

TMAO di-hydrate applied exogenously increases germination both in pre-treatment of the seeds and as an additive to the medium. Tomato 'Moneymaker' seeds were sown, grown and treated as described above.

TABLE 4

Tomato seed germination rates ± S.E. and ANOVA P-values for two independent experiments where TMAO di-hydrate effect was evaluated on seed germination under drought conditions generated by adding Polyethylene glycol (PEG-6000) to the germination medium.

| PEG CONCENTRATION | $\psi$ VALUE | NUMBER OF SEEDS | TREATMENT |
|---|---|---|---|
| 152 g/L | −0.2564 | 150 (5 × 30) | No treatment |
|  |  | 150 (5 × 30) | Pre-treatment with TMAO di-hydrate 0.1 g/L solution (3 hours) |
|  |  | 150 (5 × 30) | TMAO di-hydrate 0.1 g/L in the germination medium |
| 182 g/L | −0.3676 | 150 (5 × 30) | No treatment |
|  |  | 150 (5 × 30) | Pre-treatment with TMAO di-hydrate 0.1 g/L solution (3 hours) |
|  |  | 150 (5 × 30) | TMAO di-hydrate 0.1 g/L in the germination medium |

| PEG CONCENTRATION | GERMINATION RATE | ANOVA P-value |
|---|---|---|
| 152 g/L | 25.80 ± 4.62% | — |
|  | 70.62 ± 4.62% | 0.0000* |
|  | 71.09 ± 4.26% | 0.0000* |
| 182 g/L | 15.37 ± 3.20% | — |
|  | 18.53 ± 3.20% | 0.2310 |
|  | 45.00 ± 3.20% | 0.0086* |

Asterisks (*) indicate statistical significant differences between control and treated seeds ($\alpha=0.05$)

This example shows that TMAO can be applied exogenously in seed treatments to improve germination under drought conditions before the water stress occurs. Seeds are germinated in the presence of PEG to induce hydric stress. Two concentrations are used in the first 3 rows 152 g/L (which corresponds to a $\psi$ value of −0.2564) and a higher dose 182 g/L (which corresponds to a $\psi$ value of −0.3676) to show that at increasing values of water stress germination decreases. In the first and in the fourth rows no treatment is applied to the seeds which are germinated directly in the presence of PEG. It is shown that indeed water stress affects germination which is only of 25.80% for 152 g/L PEG (row 1) and 15.37% for 182 g/L PEG (row 4). Pre-treatment of the seeds for 3 hours with TMAO di-hydrate 0.1 g/L solution significantly increases the germination rates to 70.62% for 152 g/L PEG (row 2), and 18.53% for 182 g/L PEG (row 5) when compared to untreated controls. Furthermore if TMAO di-hydrate 0.1 g/L is added to the germination medium the germination rates significantly increase even higher to 71.09% for 152 g/L PEG (row 3), and specially to 45.00% for the higher water stress condition of 182 g/L PEG (row 6) when compared to untreated controls.

Example 5

TMAO di-hydrate applied exogenously increases plant survival in pepper under extreme drought conditions. 'Murano' pepper seeds were sown, grown and treated as described above. 10 g/L and 1 g/L TMAO di-hydrate sprayed was the best treatment when irrigation was done with water, with 83.3% of plant survival while 100% plant survival rate was observed when plants were sprayed with 0.1 g/L or 1 g/L and watered with 5 g/L.

TABLE 5

Average survival rate and ANOVA analysis for TMAO di-hydrate treated pepper plants under drought growing conditions.

| IRRIGATION | N | INITIAL SPRAY TREATMENT | SURVIVAL RATE (%) | ANOVA P-value |
|---|---|---|---|---|
| ALL REGIMES | 384 | WATER | 42.7 ± 3.6 | 0.0000 |
|  |  | 0.1 g/L TMAO | 51.0 ± 3.6 |  |
|  |  | 1 g/L TMAO | 62.5 ± 3.6 |  |
|  |  | 10 g/L TMAO | 71.8 ± 3.6 |  |
| WATER | 96 | WATER | 45.8 ± 8.1 | 0.0025 |
|  |  | 0.1 g/L TMAO | 37.5 ± 8.1 |  |
|  |  | 1 g/L TMAO | 62.5 ± 8.1 |  |
|  |  | 10 g/L TMAO | 79.1 ± 8.1 |  |
| 0.1 g/L TMAO | 96 | WATER | 29.1 ± 8.3 | 0.0000 |
|  |  | 0.1 g/L TMAO | 33.3 ± 8.3 |  |
|  |  | 1 g/L TMAO | 54.1 ± 8.3 |  |
|  |  | 10 g/L TMAO | 83.3 ± 8.3 |  |
| 1 g/L TMAO | 96 | WATER | 0.0 ± 7.7 | 0.0028 |
|  |  | 0.1 g/L TMAO | 33.3 ± 7.7 |  |
|  |  | 1 g/L TMAO | 33.3 ± 7.7 |  |
|  |  | 10 g/L TMAO | 37.5 ± 7.7 |  |
| 5 g/L TMAO | 96 | WATER | 95.8 ± 3.8 | 0.0812 |
|  |  | 0.1 g/L TMAO | 100 ± 3.8 |  |
|  |  | 1 g/L TMAO | 100 ± 3.8 |  |
|  |  | 10 g/L TMAO | 87.5 ± 3.8 |  |

Table 5 shows that TMAO can be applied exogenously by spray and/or watering before water stress occurs increasing the plant survival rate under extreme water stress conditions in a vegetable crop species. In rows 1-4 the spray treatments are compared combined independently from the irrigation treatments. The survival rate after drought significantly increases with the concentration of the TMAO spray being the lowest in row 1 without TMAO (42.7%) and the highest in row 4 with 10 g/L of TMAO (71.8%). In rows 5-8 the spray treatments are compared when the plants are irrigated only with water. Analogously survival rate after drought significantly increases with the concentration of the TMAO spray being the lowest in row 5 without TMAO (45.8%) and the highest in row 8 with 10 g/L of TMAO (79.1%). In rows 9-12 the spray treatments are compared when the plants are irrigated with 0.1 g/L of TMAO. Survival rate after drought significantly increases with the concentration of the TMAO spray being the lowest in row 9 without TMAO (29.1%) and the highest in row 12 with 10 g/L of TMAO (83.3%). In rows 13-16 the spray treatments are compared when the plants are irrigated with 1 g/L of TMAO. Survival rate after drought also significantly increases with the concentration of the TMAO spray being the lowest in row 13 without TMAO (0%) and the highest in row 16 with 10 g/L of TMAO (37.5%). The best results are achieved when plants are irrigated with TMAO at 5 g/L (rows 17-20). Even without spray treatment the survival rate is 95.8% (row 17), which increases up to 100% survival with 0.1 g/L and 1 g/L spray treatments (rows 18-19). Combining the highest doses of spray 10 g/L and irrigation 5 g/L lowers the survival rate to 87.5% (row 20) due to a TMAO overdose.

Example 6

TMAO di-hydrate applied exogenously increases plant survival in tomato under extreme drought conditions. Moneymaker tomato seeds were sown, grown and treated as described. No statistical differences between modes of application (sprayed or TMAO di-hydrate watered) were observed on this experiment. 5 g/L TMAO di-hydrate sprayed was the best treatment when irrigation was done with water, with 74.2% of plant survival. At higher test rates, both treatments showed a clear increase of shoot dry mass when compared with untreated plants. Additionally, TMAO treated plants behaved extremely healthy compared to untreated control, though plants withstand drought much better after drought treatment (FIG. 1). Additionally, as shown in FIG. 1, TMAO treated plants behaved extremely healthy compared to untreated control, though plants withstand drought much better after drought treatment. In FIG. 1, on the left-hand side control plants irrigated with water and on the right-hand side treated plants irrigated with 5.5 g/L TMAO di-hydrate after drought recovery.

TABLE 6

Average survival rate and ANOVA analysis for TMAO di-hydrate treated tomato plants under drought conditions.

| IRRIGATION | N | INITIAL SPRAY TREATMENT | SURVIVAL RATE (%) | ANOVA P-value |
|---|---|---|---|---|
| ALL REGIMES | 384 | WATER | 12.5 ± 4.1 | 0.0000 |
|  |  | 0.1 g/L TMAO | 12.5 ± 4.1 |  |
|  |  | 1 g/L TMAO | 37.5 ± 4.1 |  |
|  |  | 5 g/L TMAO | 56.6 ± 4.1 |  |
| WATER | 96 | WATER | 16.6 ± 9.1 | 0.0000 |
|  |  | 0.1 g/L TMAO | 29.1 ± 9.1 |  |
|  |  | 1 g/L TMAO | 62.5 ± 9.1 |  |
|  |  | 5 g/L TMAO | 74.2 ± 9.1 |  |
| 0.1g/L TMAO | 96 | WATER | 16.6 ± 8.5 | 0.0000 |
|  |  | 0.1 g/L TMAO | 12.5 ± 8.5 |  |
|  |  | 1 g/L TMAO | 41.6 ± 8.5 |  |
|  |  | 5 g/L TMAO | 68.9 ± 8.5 |  |
| 1 g/L TMAO | 96 | WATER | 4.1 ± 7.5 | 0.0013 |
|  |  | 0.1 g/L TMAO | 0.0 ± 7.5 |  |
|  |  | 1 g/L TMAO | 29.1 ± 7.5 |  |
|  |  | 5 g/L TMAO | 33.3 ± 7.5 |  |
| 5 g/L TMAO | 96 | WATER | 8.3 ± 8.0 | 0.0015 |
|  |  | 0.1 g/L TMAO | 12.5 ± 8.0 |  |
|  |  | 1 g/L TMAO | 16.6 ± 8.0 |  |
|  |  | 5 g/L TMAO | 50.0 ± 8.0 |  |

Table 6 shows that TMAO can be applied exogenously by spray and/or watering before the water stress occurs increasing the plant survival rate in the Solanaceae family, under extreme water stress conditions. In rows 1-4 the spray treatments are compared combined independently from the irrigation treatments. The survival rate after drought significantly increases with the concentration of the TMAO spray being the lowest in row 1 without TMAO (12.5%) and the highest in row 4 with 5 g/L of TMAO (56.6%). In rows 5-8 the spray treatments are compared when the plants are irrigated only with water. Analogously survival rate after drought significantly increases with the concentration of the TMAO spray being the lowest in row 5 without TMAO 16.6%) and the highest in row 8 with 5 g/L of TMAO (74.2%). In rows 9-12 the spray treatments are compared when the plants are irrigated with 0.1 g/L of TMAO. Survival rate after drought significantly increases with the highest concentrations of the TMAO spray being the lowest in rows 9 and 10, without TMAO (16.6%) and 0.1 g/L TMAO spray (12.5%) respectively, and the highest in row 12 with 5 g/L of TMAO (68.9%). In rows 13-16 the spray treatments are compared when the plants are irrigated with 1 g/L of TMAO. Survival rate after drought also significantly increases with the highest concentrations of the TMAO spray being the lowest in rows 13 and 14, without TMAO (4.1%) and 0.1 g/L TMAO spray (0%)

respectively, and the highest in row 16 with 5 g/L of TMAO (33.3%). Increasing the TMAO irrigation treatment to 5 g/L (rows 17-20) improves the survival rates when compared to low dose irrigation treatments combined with spray treatments, but in tomato is not as good as the spray treatments alone, probably due to a TMAO overdose, although increasing concentrations of TMAO spray still increase the overall survival rate. Combining the highest doses of spray 5 g/L and irrigation 5 g/L renders a survival rate of 50% (row 20).

Example 7

TMAO di-hydrate applied exogenously increases plant survival in cucumber under extreme drought conditions. 'Marketer' cucumber seeds were sown, grown and treated as described. Watered applications seem to produce better performance on survival rate (P value 0.05). 5 g/L TMAO sprayed was the best treatment when irrigation was done with 5 g/L TMAO, with 95.8% of plant survival.

TABLE 7

Average survival rate and ANOVA analysis for TMAO treated cucumber plants under drought growing conditions.

| IRRIGATION | N | INITIAL SPRAY TREATMENT | SURVIVAL RATE (%) | ANOVA P-value |
|---|---|---|---|---|
| ALL REGIMES | 384 | WATER | 66.6 ± 3.4 | 0.0000 |
| | | 0.1 g/L TMAO | 80.1 ± 3.4 | |
| | | 1 g/L TMAO | 92.7 ± 3.4 | |
| | | 5 g/L TMAO | 94.7 ± 3.4 | |
| WATER | 96 | WATER | 54.1 ± 7.2 | 0.0004 |
| | | 0.1 g/L TMAO | 83.3 ± 7.2 | |
| | | 1 g/L TMAO | 91.6 ± 7.2 | |
| | | 5 g/L TMAO | 95.8 ± 7.2 | |
| 0.1 g/L TMAO | 96 | WATER | 45.8 ± 7.4 | 0.0000 |
| | | 0.1 g/L TMAO | 82.9 ± 7.4 | |
| | | 1 g/L TMAO | 91.6 ± 7.4 | |
| | | 5 g/L TMAO | 95.8 ± 7.4 | |
| 1 g/L TMAO | 96 | WATER | 87.5 ± 5.9 | 0.0028 |
| | | 0.1 g/L TMAO | 91.6 ± 5.9 | |
| | | 1 g/L TMAO | 91.6 ± 5.9 | |
| | | 5 g/L TMAO | 91.6 ± 5.9 | |
| 5 g/L TMAO | 96 | WATER | 66.6 ± 7.2 | 0.0812 |
| | | 0.1 g/L TMAO | 75.0 ± 7.2 | |
| | | 1 g/L TMAO | 95.8 ± 7.2 | |
| | | 5 g/L TMAO | 95.8 ± 7.2 | |

Table 7 shows that TMAO can be applied exogenously by spray and/or watering before the water stress occurs increasing the plant survival rate in the Cucurbitaceae family, under extreme water stress conditions. In rows 1-4 the spray treatments are compared combined independently from the irrigation treatments. The survival rate after drought significantly increases with the concentration of the TMAO spray being the lowest in row 1 without TMAO (66.6%) and the highest in row 4 with 5 g/L of TMAO (94.7%). In rows 5-8 the spray treatments are compared when the plants are irrigated only with water. Analogously survival rate after drought significantly increases with the concentration of the TMAO spray being the lowest in row 5 without TMAO (54.1%) and the highest in row 8 with 5 g/L of TMAO (95.8%). In rows 9-12 the spray treatments are compared when the plants are irrigated with 0.1 g/L of TMAO. Survival rate after drought significantly increases with the concentration of the TMAO spray being the lowest in row 9 without TMAO (45.8%) and the highest in row 12 with 5 g/L of TMAO (95.8%). In rows 13-16 the spray treatments are compared when the plants are irrigated with 1 g/L of TMAO. Survival rate after drought also significantly increases with the any of the TMAO spray treatments being the lowest in row 13 without TMAO (87.5%) and higher in rows 14-16 with 0.1, 1 or 5 g/L of TMAO giving the same 91.6% survival rate. The best results are achieved when plants are irrigated with TMAO at 5 g/L (rows 17-20). Even without spray treatment the survival rate is 66.6% (row 17), which increases up to 95.8% survival with 5 g/L spray treatment (rows 20).

Example 8

TMAO di-hydrate applied exogenously increases plant survival in tomato under limited water irrigation. 'Moneymaker' tomato seeds were sown, grown and treated as described. Both spray and irrigation treatments with TMAO increased significantly plant size.

TABLE 8

Average stem size and ANOVA analysis for TMAO and water irrigated tomato plants under limited water growing conditions.

| INITIAL TREATMENT | N | IRRIGATIONS | AVERAGE STEM SIZE (cm) | ANOVA P-value |
|---|---|---|---|---|
| WATER | 94 | WATER | 10.57 ± 0.56 | 0.0000 |
| | | 1 g/L TMAO | 12.97 ± 0.55 | |
| 0.1 g/L TMAO | 93 | WATER | 11.06 ± 0.55 | 0.1034 |
| | | 1 g/L TMAO | 12.32 ± 0.56 | |
| 1 g/L TMAO | 96 | WATER | 11.59 ± 0.55 | 0.0000 |
| | | 1 g/L TMAO | 13.77 ± 0.55 | |
| 5 g/L TMAO | 92 | WATER | 14.2 ± 0.56 | 0.7230 |
| | | 1 g/L TMAO | 14.6 ± 0.55 | |

TABLE 8 shows that TMAO can be applied exogenously by spray and watering before the water stress occurs increasing the shoot biomass in the Solanaceae family, under limited water stress conditions. In rows 1-2 the irrigation treatments are compared combined independently from the spray treatments. The shoot length significantly increases after limited irrigation with 1 g/L TMAO spray being the lowest in row 1 without TMAO (10.57 cm) and the highest in row 2 with 1 g/L of TMAO spray (12.97 cm). In rows 1, 3, 5 and 7 the spray treatments are compared when the plants are irrigated only with water. Shoot length after limited water irrigation significantly increases with the concentration of the TMAO spray being the lowest in row 1 without TMAO (10.57 cm) and the highest in row 7 with 5 g/L of TMAO (14.2 cm). In rows 2, 4, 6 and 8 the spray treatments are compared when the plants are irrigated with 1 g/L of TMAO. Again shoot length significantly increases after limited water irrigation with the increasing concentrations of the TMAO spray being the lowest in row 2, without TMAO spray (12.97 cm) and the highest in row 8 when both treatments are combined with 5 g/L of TMAO spray treatment and 1 g/L irrigation treatment (14.6 cm).

Example 9

TMAO di-hydrate applied exogenously increases plant production in tomato under limited water irrigation. 'Rio Grande' tomato seeds were sown, grown and treated as described. Spray treatments with 1 g/L TMAO increased plant production.

TABLE 9

Average fruit production and ANOVA analysis for TMAO spray treated tomato plants under limited water growing conditions.

| IRRIGATION | N | INITIAL TREATMENT | AVERAGE WEIGHT (grams/fruit) | ANOVA P-value |
|---|---|---|---|---|
| 100% WATER | 36 | WATER | 73.85 ± 17.84 | — |
| 30% WATER | 36 | WATER | 52.9 ± 17.28 | 0.4243 |
| 30% WATER | 36 | 1 g/L TMAO | 76.73 ± 17.67 | 0.3406 |

Table 9 shows that TMAO can be applied exogenously by spray before the water stress occurs increasing the production in the Solanaceae family, under limited water stress conditions. In row 2 it is shown that 30% water irrigation significantly lowers plant production (52.9 g/fruit) when compared with plants in row 1 under normal water irrigation (73.85 g/fruit). However, as shown in row 3, spray treatment with 1 g/L of TMAO di-hydrate applied exogenously every 4 weeks restores plant production with an increase of fruit production of 45% even under limited water irrigation (76.73 g/fruit) over the untreated plants with a 30% irrigation.

Example 10

TMAO di-hydrate applied exogenously increases plant survival and biomass in barley under limited water irrigation. 'Bomi' barley seeds were sown, grown and treated as described.

TABLE 10

Average dry weight ± S.E. and ANOVA analysis for TMAO di-hydrate and water irrigated barley plants under drought growing conditions.

| INITIAL TREATMENT | N | IRRIGATIONS | AVERAGE DRY WEIGHT (mg) | ANOVA P-value |
|---|---|---|---|---|
| CONTROL | 10 | WATER | 1017.7 ± 66.13 | — |
| 1 g/L SPRAYED TMAO di-hydrate SOLUTION | 12 | WATER | 1205.4 ± 60.37 | 0.0212* |
| 1 g/L WATERED TMAO di-hydrate SOLUTION | 10 | WATER | 1371.4 ± 66.13 | 0.0073* |
| — | 70 | CONTROL | 1109.3 ± 33.93 | — |
| — | 68 | 1 g/L TMAO di-hydrate SOLUTION | 1216.1 ± 33.44 | 0.0265* |

Table 10 shows that TMAO can be applied exogenously by spray and watering before the water stress occurs increasing the plant survival rate and shoot biomass in monocotyledonous plants, under extreme water stress conditions. In the first three rows the initial treatments are compared, both 1 g/L TMAO di-hydrate spray (row 2) and 1 g/L TMAO di-hydrate irrigation treatments (row 3) significantly increase the mean dry biomass per plant, under extreme drought conditions, to 1205.4 mg and 1371.4 respectively when compared with water treated control plants in row 1 (1017.7 mg). Furthermore, analogous results can be obtained when plants are only irrigated with 1 g/L TMAO di-hydrate (row 5: 1216.1 mg per plant) when compared with the same amount of limited irrigation with water without TMAO in row 4 (1109.3 mg).

Example 11

TMAO di-hydrate applied exogenously increases plant production in corn under limited water irrigation. 'FAO700' corn seeds were sown, grown and treated as described. Spray treatments with 1 g/L TMAO increased plant number of green leaves, total chlorophyll content and grain production.

TABLE 11

Average number of green leaves and ANOVA analysis for TMAO spray or seed treated corn plants under limited water growing conditions.

| IRRIGATION REGIME | N | TREATMENT | AVERAGE NUMBER OF GREEN LEAVES | P VALUE |
|---|---|---|---|---|
| 100% WATER | 30 | — | 11.03 ± 0.33 | — |
| 30% WATER | 23 | — | 5.78 ± 0.38 | — |
| 30% WATER | 53 | 1 g/L TMAO SPRAY | 8.50 ± 0.25 | 0.0000* |
| 30% WATER | 20 | 1 g/L TMAO SEED | 8.50 ± 0.41 | 0.0001* |

Table 11 shows that TMAO can be applied exogenously by spray before the water stress occurs, or by seed incubation, increasing the biomass production in the monocotyledonous plants, under limited water stress conditions. In row 2 it is shown that 30% water irrigation significantly lowers the number of green leaves when compared with plants in row 1 under normal water irrigation. However, as shown in rows 3 and 4, spray treatment with 1 g/L of TMAO di-hydrate when applied exogenously every 4 weeks significantly restores the number of green leaves under limited water irrigation with a 47% increase in biomass production, shown in green leaf production over the untreated plants with a 30% irrigation.

Example 12

TMAO di-hydrate applied exogenously increases plant production in corn under limited water irrigation. 'TAO700" corn seeds were sown, grown and treated as described above. As shown in Table 12, spray treatments with 1 g/L TMAO increased plant total chlorophyll content.

TABLE 12

Average chlorophyll content and ANOVA analysis for TMAO spray or seed treated corn plants under limited water growing conditions.

| IRRIGATION REGIME | N | TREATMENT | TOTAL CHLOROPHYL CONTENT | P VALUE |
|---|---|---|---|---|
| 100% WATER | 30 | — | 0.9163 ± 0.052 | — |
| 30% WATER | 23 | — | 0.5194 ± 0.107 | — |
| 30% WATER | 53 | 1g/L TMAO SPRAY | 0.7278 ± 0.076 | 0.1214 |
| 30% WATER | 20 | 1g/L TMAO SEED | 0.8977 ± 0.195 | 0.1854 |

Table 12 shows that TMAO can be applied exogenously by spray before the water stress occurs, or by seed incubation, increasing the biomass production in the monocotyledonous plants, under limited water stress conditions. In row 2 it is shown that 30% water irrigation significantly lowers total chlorophyll content when compared with plants in row 1 under normal water irrigation. However, as shown in rows 3 and 4, spray treatment with 1 g/L of TMAO di-hydrate when applied exogenously every 4 weeks significantly restores the chlorophyll content under limited water irrigation with an increase in biomass production between 40% and 72%, shown in chlorophyll content over the untreated plants with a 30% irrigation.

Example 13

TMAO di-hydrate applied exogenously increases plant production in corn under limited water irrigation. 'TAO700" corn seeds were sown, grown and treated as described. Spray treatments with 1 g/L TMAO increased plant grain production.

TABLE 13

Average number of grains per cob and ANOVA analysis for TMAO spray or seed treated corn plants under limited water growing conditions.

| IRRIGATION REGIME | N | TREATMENT | AVERAGE NUMBER OF GRAINS PER COB | P VALUE |
| --- | --- | --- | --- | --- |
| 100% WATER | 30 | — | 533.95 ± 22.48 | — |
| 30% WATER | 23 | — | 429.13 ± 45.31 | — |
| 30% WATER | 53 | 1 g/L TMAO SPRAY | 511.34 ± 19.70 | 0.0495* |
| 30% WATER | 20 | 1 g/L TMAO SEED | 542.89 ± 41.22 | 0.0757 |

Table 13 shows that TMAO can be applied exogenously by spray before the water stress occurs, or by seed incubation, increasing the biomass production in the monocotyledonous plants, under limited water stress conditions. In row 2 it is shown that 30% water irrigation significantly lowers total number of grains per corn cob when compared with plants in row 1 under normal water irrigation. However, as shown in rows 3 and 4, spray treatment with 1 g/L of TMAO di-hydrate when applied exogenously every 4 weeks significantly restores the total number of grains per corn cob under limited water irrigation with an increase in biomass production between 19% and 27%, shown in chlorophyll content over the untreated plants with a 30% irrigation. Of note, row 4 actually shows a 2% increase in the total number of grains per corn cob for corn plants under 30% water irrigation with a spray treatment of 1 g/L of TMAO di-hydrate when compared to corn plants with no water stress or 100% irrigation.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

What is claimed is:

1. A method for producing a drought tolerant plant, or plant part comprising:
   applying at least one treatment consisting of an effective amount of trimethylamine N-oxide di-hydrate solution to a plant, or plant part, wherein said effective amount of trimethylamine N-oxide di-hydrate solution is between 1 g and 10 g trimethylamine N-oxide di-hydrate per liter of water and 0.1% alkylpolysaccharide, wherein said effective amount of said trimethylamine N-oxide di-hydrate solution is sufficient to induce drought tolerance to said plant, or plant part; and
   growing said plant, or plant part, wherein a drought tolerant plant is produced.

2. A method for producing a drought tolerant plant, or plant part comprising:
   applying at least one treatment consisting of an effective amount of trimethylamine N-oxide di-hydrate solution to a plant, or plant part, wherein said effective amount of trimethylamine N-oxide di-hydrate solution is between 1 g and 10 g trimethylamine N-oxide di-hydrate per liter of water, wherein said effective amount of said trimethylamine N-oxide di-hydrate solution is sufficient to induce drought tolerance to said plant, or plant part; and
   growing said plant, or plant part, wherein a drought tolerant plant is produced.

3. The method of claim 2 further comprising:
   applying a second or more treatment of the effective amount of trimethylamine N-oxide di-hydrate solution to said drought tolerant plant, or plant part, wherein said effective amount of trimethylamine N-oxide di-hydrate solution is sufficient to maintain drought tolerance to said plant, or plant part.

4. The method of claim 2, wherein said at least one treatment of said effective amount of trimethylamine N-oxide di-hydrate solution is an irrigation treatment or a spray treatment.

5. The method of claim 1, wherein said at least one treatment of the effective amount of trimethylamine N-oxide di-hydrate solution to a plant or plant part is sufficient to increase trimethylamine N-oxide levels in said plant or plant part at least 5 fold compared to non-tolerant drought stressed plants where the effective amount of trimethylamine N-oxide di-hydrate solution sufficient to induce drought tolerance in a plant has not been applied to the non-tolerant drought stressed plant.

6. The method of claim 2 wherein said at least one treatment of the effective amount of trimethylamine N-oxide di-hydrate solution to a plant or plant part is sufficient to increase trimethylamine N-oxide levels in said plant or plant part at least 3 fold compared to non-tolerant drought stressed plants where the effective amount of trimethylamine N-oxide di-hydrate solution sufficient to induce drought tolerance in a plant has not been applied to the non-tolerant drought stressed plant.

7. The method of claim 1, wherein said plant or plant part is selected from the group consisting of barley, tomato, pepper, corn, canola, sunflower, broccoli, strawberry, and wheat.

8. The method of claim 2, wherein said drought tolerant plant has a biomass production that is 5% greater than the biomass production of non-tolerant drought stressed plants where the effective amount of trimethylamine N-oxide di-hydrate solution sufficient to induce drought tolerance in a plant has not been applied to the non-tolerant drought stressed plant.

9. The method of claim 2, wherein said drought tolerant plant has a biomass production that is between 5% and 19% greater than the biomass production of non-tolerant drought stressed plants where the effective amount of trimethylamine N-oxide di-hydrate solution sufficient to induce drought tolerance in a plant has not been applied to the non-tolerant drought stressed plant.

10. The method of claim 2, wherein said drought tolerant plant has a biomass production that is between 19% and 30% greater than the biomass production of non-tolerant drought stressed plants where the effective amount of trimethylamine N-oxide di-hydrate solution sufficient to induce drought tolerance in a plant has not been applied to the non-tolerant drought stressed plant.

11. The method of claim 2, wherein said drought tolerant plant has a biomass production that is between 31% and 50% greater than the biomass production of non-tolerant drought stressed plants where the effective amount of trimethylamine N-oxide di-hydrate solution sufficient to induce drought tolerance in a plant has not been applied to the non-tolerant drought stressed plant.

12. The method of claim 2, wherein said drought tolerant plant has a biomass production that is between 51% and 70% greater than the biomass production of non-tolerant drought stressed plants where the effective amount of trimethylamine N-oxide di-hydrate solution sufficient to induce drought tolerance in a plant has not been applied to the non-tolerant drought stressed plant.

13. The method of claim 2, wherein said drought tolerant plant has a biomass production that is between 71% and 100% greater than the biomass production of non-tolerant drought stressed plants where the effective amount of trimethylamine N-oxide di-hydrate solution sufficient to induce drought tolerance in a plant has not been applied to the non-tolerant drought stressed plant.

14. A method for producing a drought tolerant plant, or plant part comprising:
applying a first treatment consisting of an effective amount of trimethylamine N-oxide di-hydrate solution to a plant, or plant part, wherein said effective amount of trimethylamine N-oxide di-hydrate solution is between 0.1 g and 1 g trimethylamine N-oxide di-hydrate per liter of water;
applying a second or more treatment consisting of an effective amount of trimethylamine N-oxide di-hydrate solution to a plant, or plant part, wherein said second or more treatment of an effective amount of trimethylamine N-oxide di-hydrate solution is between 0.1 g and 10 g trimethylamine N-oxide di-hydrate per liter of water, wherein said first and second or more treatments are sufficient to induce drought tolerance to said plant, or plant part; and
growing said plant, or plant part, wherein a drought tolerant plant is produced.

15. The method of claim 14, wherein said first treatment is a spray treatment and wherein said second or more treatment is an irrigation treatment.

16. A method for producing a drought tolerant plant seed comprising:
applying at least one treatment consisting of an effective amount of trimethylamine N-oxide di-hydrate solution to at least one plant seed, wherein said effective amount of trimethylamine N-oxide di-hydrate solution is between 0.1 g and 1 g trimethylamine N-oxide di-hydrate per liter of water, wherein said effective amount of said trimethylamine N-oxide di-hydrate solution is sufficient to induce drought tolerance in said plant seed.

17. The method of claim 16, wherein the effective amount of said trimethylamine N-oxide di-hydrate solution is sufficient increase the germination rate of said plant seed by at least 15%.

18. The method of claim 16 further comprising growing said drought tolerant seed and producing a drought tolerant plant, wherein said drought tolerant plant has a biomass production that is 5% greater than the biomass production of non-tolerant drought stressed plants where the effective amount of trimethylamine N-oxide di-hydrate solution sufficient to induce drought tolerance in a seed was not applied to the non-tolerant drought stressed seed.

19. The method of claim 16 further comprising growing said drought tolerant seed and producing a drought tolerant plant, wherein said drought tolerant plant has a biomass production that is between 5% and 19% greater than the biomass production of non-tolerant drought stressed plants where the effective amount of trimethylamine N-oxide di-hydrate solution sufficient to induce drought tolerance in a seed was not applied to the non-tolerant drought stressed seed.

20. The method of claim 16 further comprising growing said drought tolerant seed and producing a drought tolerant plant, wherein said drought tolerant plant has a biomass production that is between 19% and 30% greater than the biomass production of non-tolerant drought stressed plants where the effective amount of trimethylamine N-oxide di-hydrate solution sufficient to induce drought tolerance in a seed was not applied to the non-tolerant drought stressed seed.

21. The method of claim 16 further comprising growing said drought tolerant seed and producing a drought tolerant plant, wherein said drought tolerant plant has a biomass production that is between 31% and 50% greater than the biomass production of non-tolerant drought stressed plants where the effective amount of trimethylamine N-oxide di-hydrate solution sufficient to induce drought tolerance in a seed was not applied to the non-tolerant drought stressed seed.

22. The method of claim 16 further comprising growing said drought tolerant seed and producing a drought tolerant plant, wherein said drought tolerant plant has a biomass production that is between 51% and 70% greater than the biomass production of non-tolerant drought stressed plants where the effective amount of trimethylamine N-oxide di-hydrate solution sufficient to induce drought tolerance in a seed was not applied to the non-tolerant drought stressed seed.

23. The method of claim 16 further comprising growing said drought tolerant seed and producing a drought tolerant plant, wherein said drought tolerant plant has a biomass production that is between 71% and 100% greater than the biomass production of non-tolerant drought stressed plants where the effective amount of trimethylamine N-oxide di-hydrate solution sufficient to induce drought tolerance in a seed was not applied to the non-tolerant drought stressed seed.

24. The method of claim 16, wherein said plant seed is selected from the group consisting of tomato seed, corn seed, pepper seed, barley seed, cucumber seed, canola seed, sunflower seed, broccoli seed, and wheat seed.

25. The method of claim 2, wherein said plant or plant part is selected from the group consisting of barley, tomato, pepper, corn, canola, sunflower, broccoli, strawberry, and wheat.

26. A method for producing a drought tolerant plant seed comprising:

Applying at least two treatments consisting of an effective amount of trimethylamine N-oxide di-hydrate to at least one plant seed, wherein said effective amount of trimethylamine N-oxide is between 0.1 g and 1 g trimethylamine N-oxide di-hydrate per liter of solution, and wherein said effective amount of said trimethylamine N-oxide is sufficient to induce drought tolerance in said plant seed.

* * * * *